(12) United States Patent
Brownell et al.

(10) Patent No.: US 9,676,520 B2
(45) Date of Patent: Jun. 13, 2017

(54) DATA STORAGE DEVICE WITH INTEGRATED BIO-STORAGE MEDIA

(71) Applicant: GENISYSS, LLC, Goleta, CA (US)

(72) Inventors: Richard A. Brownell, Lompoc, CA (US); Mitchell Frey, Santa Barbara, CA (US)

(73) Assignee: GENISYSS, LLC, Goleta, CA (US)

( * ) Notice: Subject to any disclaimer, the term of this patent is extended or adjusted under 35 U.S.C. 154(b) by 951 days.

(21) Appl. No.: 13/764,383

(22) Filed: Feb. 11, 2013

(65) Prior Publication Data

US 2013/0146488 A1    Jun. 13, 2013

Related U.S. Application Data

(63) Continuation-in-part of application No. 12/605,618, filed on Oct. 26, 2009, now Pat. No. 8,806,127.

(51) Int. Cl.
| | |
|---|---|
| *B01L 3/00* | (2006.01) |
| *B65D 25/00* | (2006.01) |
| *G06F 19/28* | (2011.01) |

(52) U.S. Cl.
CPC ............ *B65D 25/00* (2013.01); *G06F 19/28* (2013.01)

(58) Field of Classification Search
CPC ............................ B01L 2300/0816; B01L 9/52
USPC .................................................. 422/554, 552
See application file for complete search history.

(56) References Cited

U.S. PATENT DOCUMENTS

| | | |
|---|---|---|
| 3,970,996 A | 7/1976 | Yasaka et al. |
| 5,496,562 A | 3/1996 | Burgoyne |
| 5,756,126 A | 5/1998 | Burgoyne |
| 5,807,527 A | 9/1998 | Burgoyne |
| 5,972,386 A | 10/1999 | Burgoyne |
| 5,985,327 A | 11/1999 | Burgoyne |
| 6,140,936 A | 10/2000 | Armstrong |
| 6,187,269 B1 * | 2/2001 | Lancesseur ............ B01L 3/502 422/401 |
| 6,241,689 B1 | 6/2001 | Chard et al. |
| 6,285,285 B1 | 9/2001 | Mongrenier |
| 6,346,886 B1 | 2/2002 | De La Huerga |
| 6,513,720 B1 | 2/2003 | Armstrong |
| 6,840,911 B2 | 1/2005 | Sangha |
| 7,142,987 B2 | 11/2006 | Eggers |
| 7,216,802 B1 | 5/2007 | De La Huerga |
| 7,485,499 B2 | 2/2009 | Brewer et al. |
| 2003/0129755 A1 | 7/2003 | Sadler et al. |
| 2004/0101966 A1 | 5/2004 | Davis et al. |
| 2004/0161855 A1 * | 8/2004 | Kvasnik ................. B01L 3/545 436/165 |
| 2005/0276728 A1 * | 12/2005 | Muller-Cohn ........... A01N 1/00 422/400 |

(Continued)

*Primary Examiner* — Natalia Levkovich
(74) *Attorney, Agent, or Firm* — McKee, Voorhees & Sease, PLC

(57) ABSTRACT

A storage device includes a housing, a non-volatile memory disposed within the housing, and an interface operatively connected to the housing for communicating with a computing device to provide access to the non-volatile memory to the computing device. The storage device further includes a tray comprising a bio-sample storage area for storing bio-samples and a gasket for sealing the bio-sample storage area within the housing for storage. In a closed position, the tray is sealed within the housing by the gasket and wherein in an open position, the bio-sample storage area is exposed and accessible.

16 Claims, 14 Drawing Sheets

(56) References Cited

U.S. PATENT DOCUMENTS

2008/0069407 A1 3/2008 Kocher
2008/0250193 A1 10/2008 Smith
2009/0062677 A1 3/2009 Bolonkin

* cited by examiner

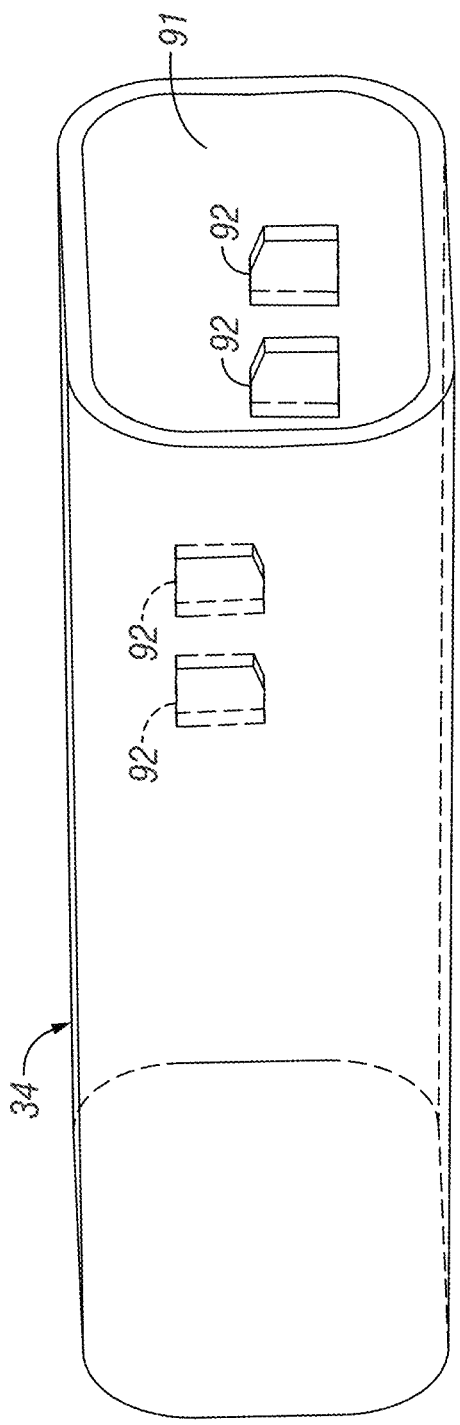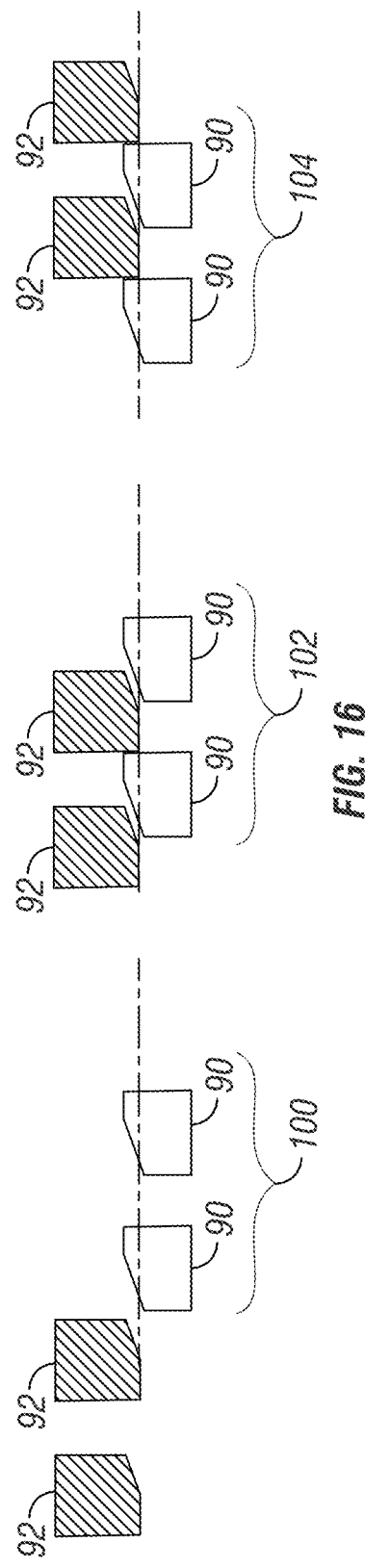

DATA STORAGE DEVICE WITH INTEGRATED BIO-STORAGE MEDIA

PRIORITY STATEMENT

The present application is a continuation-in-part of and claims priority to U.S. patent application Ser. No. 12/605,618, filed Oct. 26, 2009, hereby incorporated by reference in its entirety.

FIELD OF THE INVENTION

This application relates generally to the field of bio-sample storage and identification, and more particularly to an integrated device with digital storage memory for data and bio-storage.

BACKGROUND OF THE INVENTION

Bio-sampling has become increasingly important in numerous fields. Bio-samples may include DNA, RNA, viral, or other types of material. Bio-samples may be collected from blood, saliva, semen, cell tissues, including plant, human, and animal, and other types of biological material. DNA and sampling of DNA have become increasingly important in numerous fields from law enforcement and forensic science to species monitoring. With an estimated 400,000 DNA samples taken daily, with many competing forms of both physical DNA and associated data storage, the issues of use, transportation and storage make establishing standardized packages a difficult problem. Physical DNA samples and associated data files have been maintained physically separated due to the storage environment and physical configurations required. Such separate storage is problematic from the standpoint of potential loss or damage of tracking information and high cost of retrieval. With the volume of DNA information being retained, the sheer size of information files requires enormous temperature and humidity-controlled environments for file storage at significant cost to maintain. Additionally, cold DNA storage requires complex and expensive facility infrastructure, consuming considerable energy to maintain sample viability.

As exemplary, the Child Identification safety market is burgeoning with products using such elements as hair clippings or buccal swabs for DNA without sufficient long term storage survivability or reliable matching of associated data. In Forensic science, DNA samples are collected and stored separately from photographs, notes and other physical or digital evidence adding to the complexity of the chain of evidence.

It is therefore desirable to provide for integrated storage of bio-samples and associated data in a room temperature storable device. It is further desirable that the integrated storage system be small and compatible with existing computer and data storage systems.

SUMMARY OF THE INVENTION

Exemplary embodiments provide an integral digital memory storage device having a standard form factor to be received by and communicating with a computing device and having memory capability for storage of digital data. An integral multi-well bio-sample tray is carried in a body of the memory storage device for protection and exposed by manipulation of the case for receiving bio-samples.

In one configuration the integrated storage unit is housed in a SD form factor flash card. In an alternative configuration, the integrated storage unit is housed in a USB thumb drive case.

A system for storage of bio-samples and corresponding digital data incorporates a standard form factor case with memory for storage of digital data. An integral bio-sample tray is carried in a body of the case for protection said tray exposed by manipulation of the case for receiving bio-samples. A computer is employed having an interface to receive the standard form factor case and at least one data entry device connected to the computer. Operating software associated with the computer downloads data from the entry device into the memory. The data entry device in various configurations may be a keyboard, a camera, an image scanner, a fingerprint scanner, a network interface and a computer memory.

The various embodiments may be employed in a method wherein a bio-sample is obtained and transferred to the sample tray. The integrated storage unit is inserted into an interface on the computing device and a unique indicia is identified associated with the integrated storage unit. Data associated with the bio-sample is then input into the computer and downloaded from the computer into the memory of the integrated storage unit. The integrated storage unit is then removed from the computer.

According to another aspect, a storage device is provided. The storage device includes a housing, a non-volatile memory disposed within the housing, and an interface operatively connected to the housing for communicating with a computing device to provide access to the non-volatile memory to the computing device. The storage device further includes a tray comprising a bio-sample storage area for storing bio-samples and a gasket for sealing the bio-sample storage area within the housing for storage. In a closed position, the tray is sealed within the housing by the gasket and wherein in an open position, the bio-sample storage area is exposed.

According to another aspect, a storage device is provided which includes a housing, a non-volatile memory disposed within the housing, and an interface operatively connected to the housing for communicating with a computing device to provide access to the non-volatile memory to the computing device. The storage device further includes a tray comprising a bio-sample storage area for storing bio-samples, a plurality of wells within the tray, dry storage media within each of the plurality of wells, a desiccant disposed within the housing for drying air within the housing, and a plurality of holes within the tray to assist in providing air flow.

According to yet another aspect, a storage device includes a housing, a non-volatile memory disposed within the housing, an interface operatively connected to the housing for communicating with a computing device to provide access to the non-volatile memory to the computing device, a tray comprising a bio-sample storage area for storing bio-samples, a plurality of wells within the tray, dry storage media within each of the plurality of wells, a desiccant disposed within the housing for drying air within the housing, and a gasket for sealing the bio-sample storage area within the housing for storage. In a closed position, the tray is sealed within the housing by the gasket and in an open position, the bio-sample storage area is exposed and accessible. The storage device further includes a plurality of interlocking pins on an interior wall of the housing and a plurality of interlocking pins on the tray to interlock to lock the tray within the housing in the closed position.

The features, functions, and advantages that have been discussed can be achieved independently in various embodiments of the present invention or may be combined in yet other embodiments further details of which can be seen with reference to the following description and drawings.

BRIEF DESCRIPTION OF THE DRAWINGS

FIG. 15 further illustrates interlocking pins on opposite sides of the interior of the cover of the device.

FIG. 16 illustrates operation of interlocking pins.

DETAILED DESCRIPTION OF THE PREFERRED EMBODIMENTS

Embodiments of the invention incorporate a structure for bio-sample and data storage which provides physical media for retaining bio-samples integrally stored within the case of a digital memory device capable of storing accompanying data regarding the samples.

Figure 1:
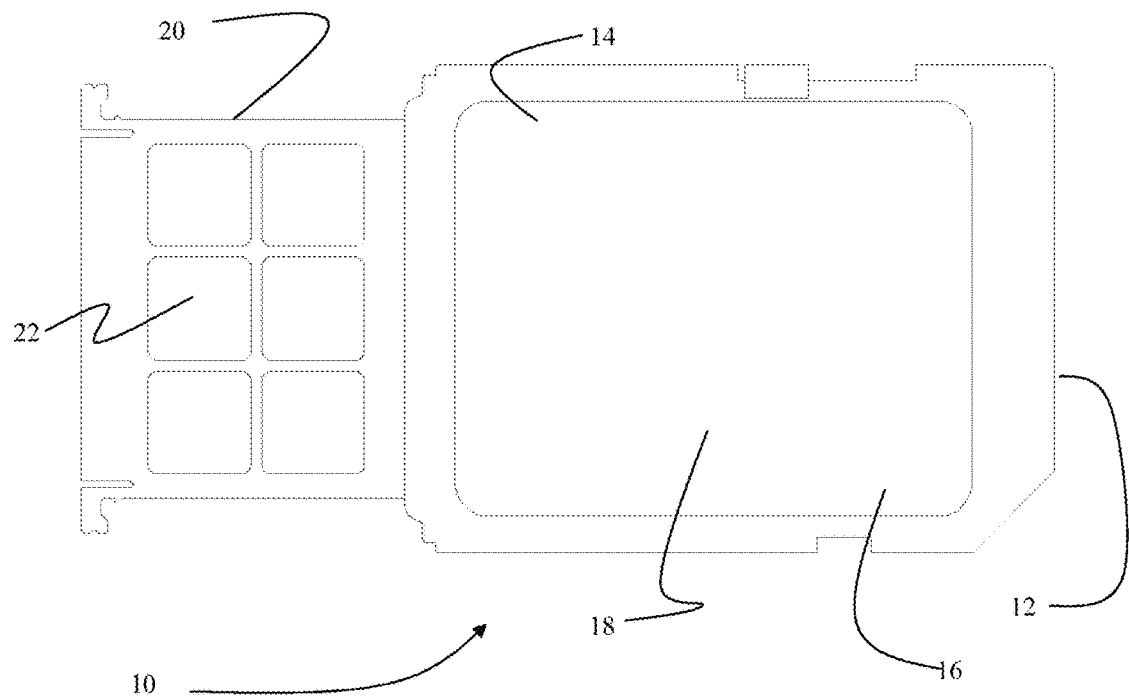
FIG. 1 is a top view of a SD flash form factor implementation of the invention with the multi-well bio-sample drawer in the open position.
Figure 2A:
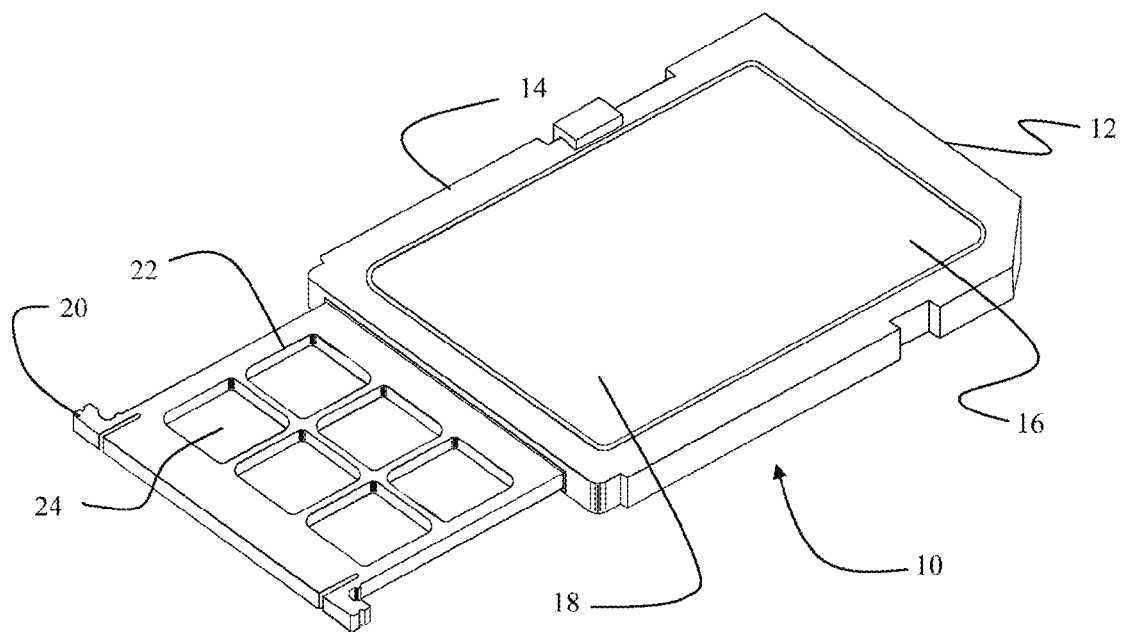
FIG. 2A is an isometric view of the embodiment of FIG. 1 with the sample tray in the open position.
Figure 2B:
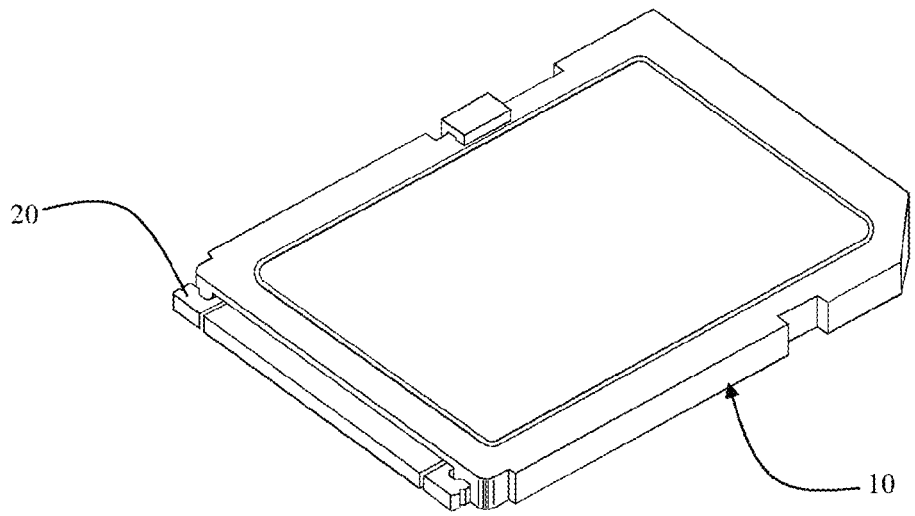
FIG. 2B is an isometric view of the embodiment of FIG. 2 with the sample tray in the closed position.
Figure 3:
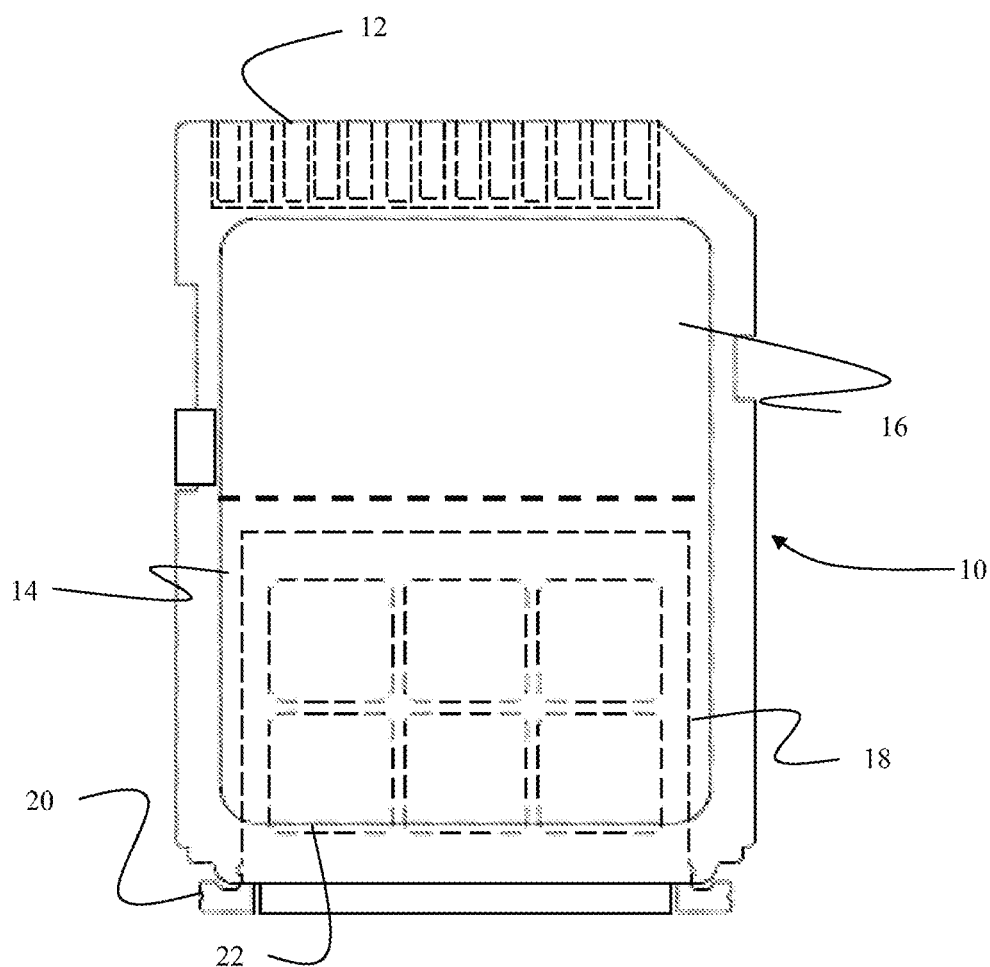
FIG. 3 is a top hidden line view of the embodiment of FIG. 1 with the sample drawer in the closed position and internal details shown.

As shown in FIGS. 1-3, a first embodiment of an integrated digital data and bio-sample storage unit (the "integrated storage unit") employs a memory device having a form factor to be received in a standard interface for a SD flash card. The flash card 10 has a standard case profile with data transfer pins 12. A body 14 of the card includes portion 16 for the microelectronics for the digital memory and a portion 18 receiving an extendible tray 20. The tray incorporates multiple wells 22 each having a nano-fiber dry storage media (such as FTA® paper available from Whatman Group) 24 for storing of DNA or other bio-samples which may be applied to the FTA® in a conventional manner with the tray in the extended position as shown in FIG. 2A. Other types of media may be used including various other types of bio-sample paper or filter paper or other dry storage media. The tray may then be depressed into the receiving portion of the case to protect the bio-sample media as shown in FIG. 2B. FIG. 3 shows the case in the closed position with the internal details shown in hidden line view. For the embodiment shown, multiple wells are shown for bio-sample storage in the tray. In alternative embodiments, a single well and/or multiple horizontally or vertically stacked trays with multiple or single wells on one or both sides of the tray may be employed using FTA® paper or other nano-fiber or other room temperature dry storage media for bio-sample storage.

Figure 4:
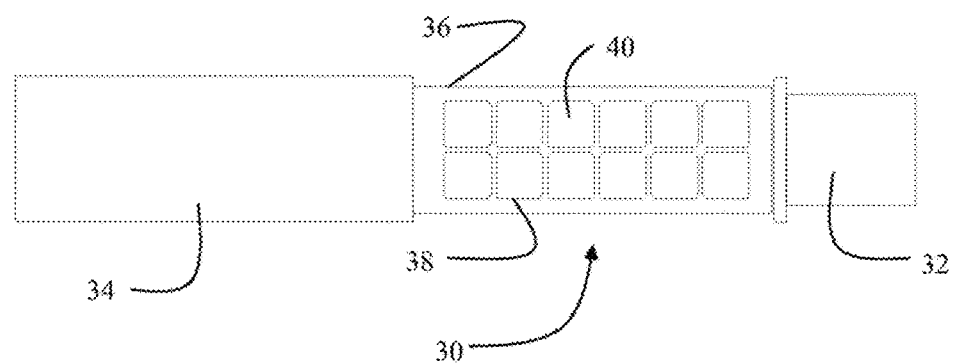
FIG. 4 is a top view of a second embodiment employing a USB thumb drive form factor with the case in the open position.
Figure 5:
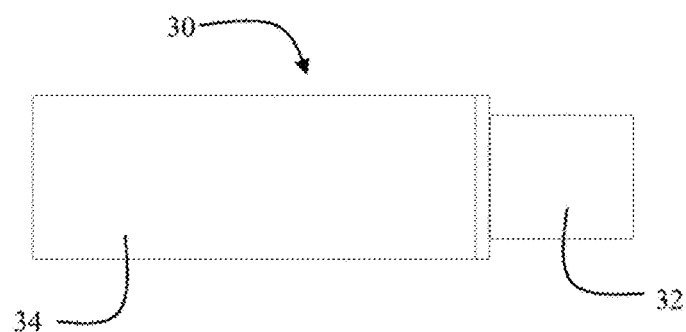
FIG. 5 is a top view of the second embodiment with the case in the closed position.
Figure 6:
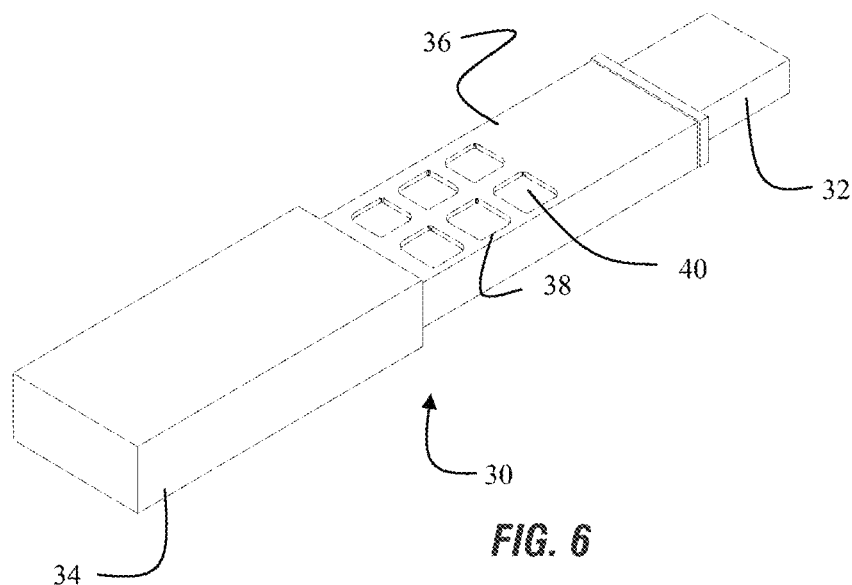
FIG. 6 is an isometric view of FIG. 4.
Figure 7:
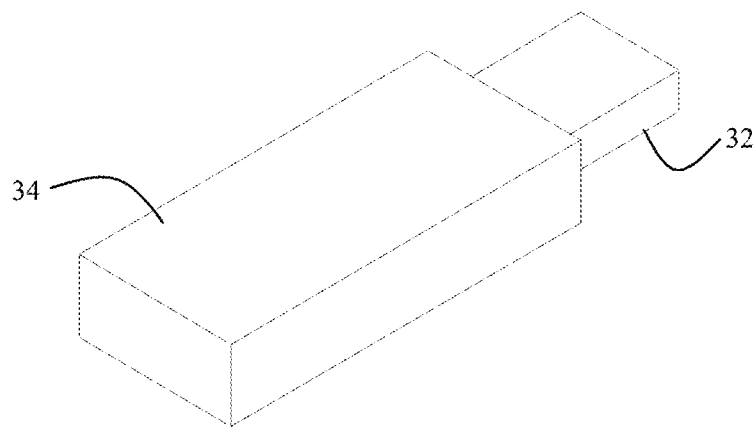
FIG. 7 is an isometric view of FIG. 5.

FIGS. 4-7 show an alternative embodiment wherein the memory device is a standard USB Thumb Drive configuration. The integrated storage unit employs a USB thumb drive 30 which has a standard USB interface 32. As shown in FIGS. 4 and 6, a sliding removable case cover 34 is withdrawn to expose a tray 36 incorporating multiple wells 38 each having a dry storage media such as nano-fiber dry storage media (FTA® paper) 40 for storing of a DNA or other type of bio-sample which may be deposited onto the paper storage media in a conventional manner with the case cover removed. The well cavity is then received into the case cover for complete encapsulation of the paper storage media to protect the samples as shown in FIGS. 5 and 7.

The integrated storage unit is advantageous in that it allows for both bio-samples and data to be stored in a single device. In addition, due to the manner in which the bio-samples are stored, namely on dry storage media, it allows the bio-samples to be stored without requiring cold storage or a refrigerated environment, and allows for storage even at room temperature. Room temperature is generally considered to be a temperature within the range of about 59° to about 77° F. (about 15° to about 25° C.). Although the integrated storage unit may be stored at room temperature, it may be stored at cooler or even warmer temperatures as well.

Figure 10:
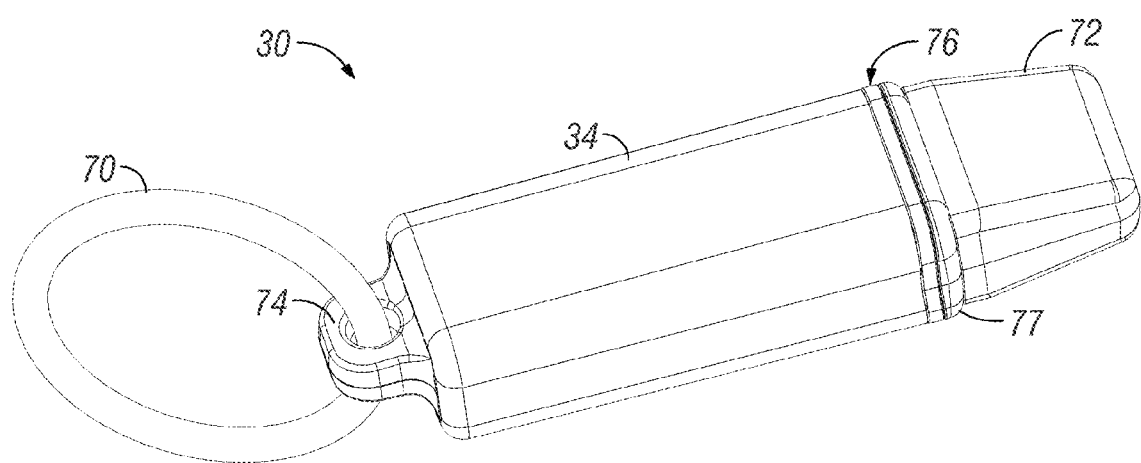
FIG. 10 is a perspective view of another embodiment in a closed position.

FIG. 10 illustrates another view of an embodiment of an integrated storage unit 30 in a closed position. The integrated storage unit 30 has a key ring 70 extending through a key ring hole 74 at one end of the integrated storage unit 30 and an end cap 72 at an opposite end. A portion of a gasket 76 presses against a shoulder 77 to form a seal.

Figure 11:
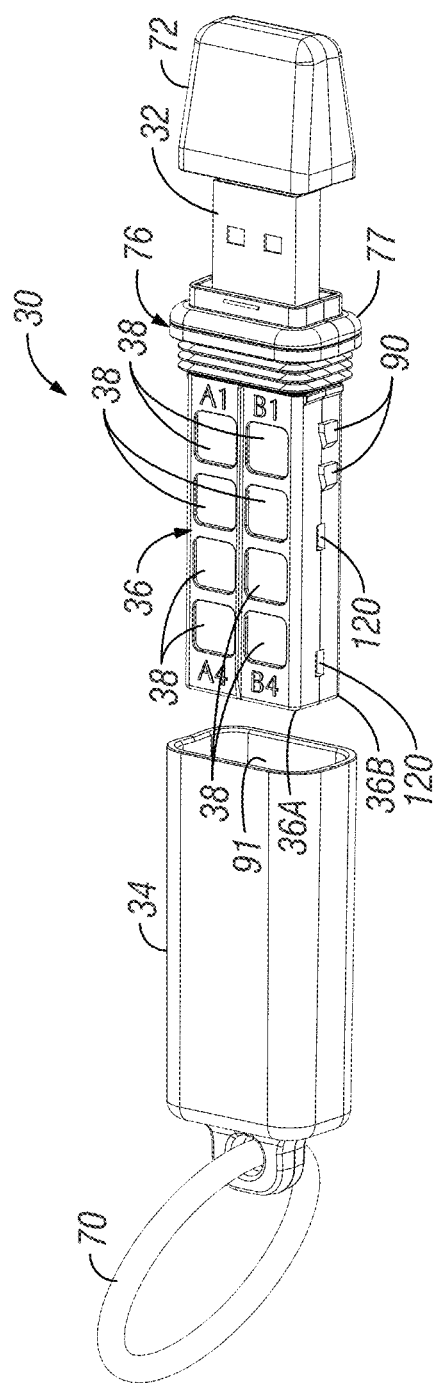
FIG. 11 is a perspective view of the embodiment of FIG. 10 in an open position.

FIG. 11 illustrates the integrated storage unit 30 in an open position. There are interlocking pins 90 on opposite sides of the tray 36 which interlock with opposing pins within the chamber 91 disposed within the case cover 34. In addition, the tray 36 has a top shell 36A and a bottom shell 36B and air vent holes 120 are shown.

The interface 32 allows the device 30 need not be a USB interface or SD interface but may be another type of interface. In addition, the memory associated with the interface 32 is a nonvolatile memory of any number of types using any number of different technologies including, but not limited to memory using technologies such as flash, ferroelectric, magnetic, laser, optical, hologram, crystallographic phase change, molecular, DNA, or other types of nonvolatile memory.

Figure 12:
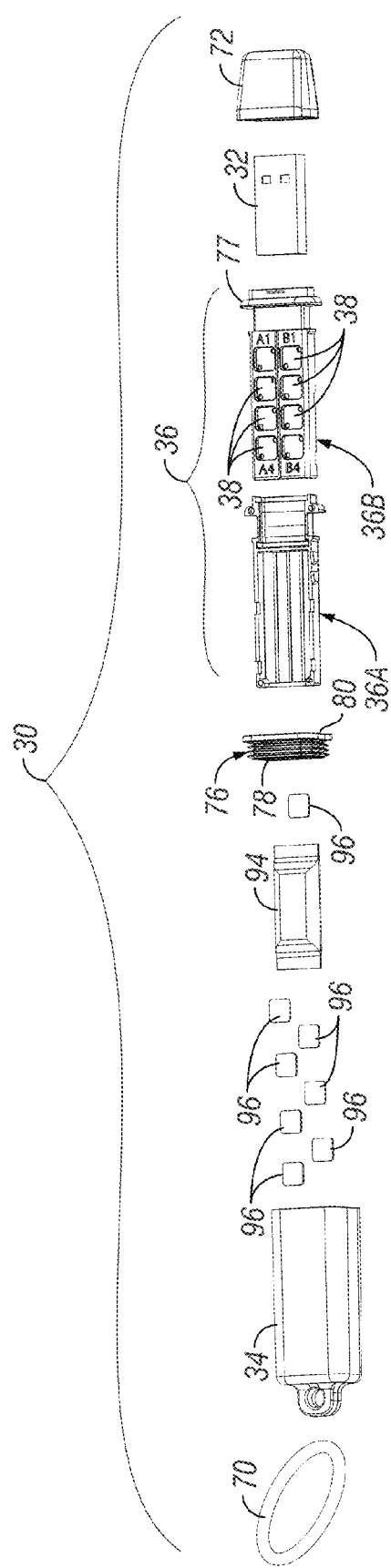
FIG. 12 is an exploded view of the embodiment shown in FIG. 10 and FIG. 11.

FIG. 12 illustrates an exploded view of the integrated storage unit 30. Note that a desiccant pack 94 is shown which may be placed in the integrated storage unit 30 to protect against moisture. Although a pillow type desiccant pack 94 is shown, other size and shapes of desiccant may be used and various types of materials may be used. Various types of desiccant material may include: charcoal, Silica Gel, Calcium Oxide, molecular sieve, clays, and others. The shape or form can be a packet, solid block, sintered, or even loose particles (if sufficiently large enough to be retained). Air paths are designed to dry samples as fast as possible. The device may include paths for air above and below the material. Note the holes in the well bottoms, and the slots on the sides of the shells 36A, 36B both facilitate airflow and sample moisture removal.

Figure 13:
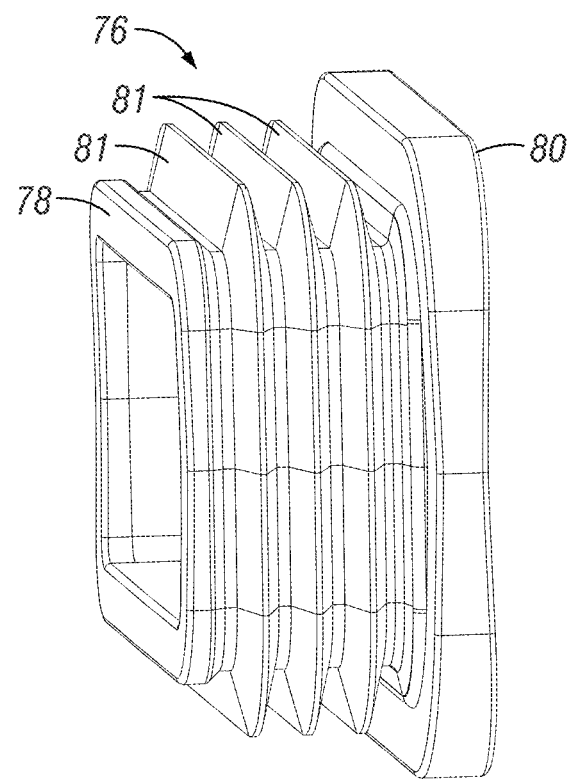
FIG. 13 is a perspective view of one embodiment of a gasket used in the device.

FIG. 13 is a perspective view of the gasket 76 with opposite ends 80, 78. One type of material that may be used for the gasket is silicone. A silicone gasket may survive intact over decades without serious deformation, drying, cracking or other degradation that may compromise the sealed environment inside the device. The gasket 76 serves as the spring of the cover/locking mechanism and thus supports multiple functions. The gasket 76 has redundant ribs 81 that help insure sealing the chamber in the event a rib gets torn or otherwise compromised. The space between the ribs 81 also allows for compression such that the cover can rotate a sufficient amount to operate the locking mechanism. As best shown in FIG. 11, the gasket 76 is placed directly over a "potting area" specifically designed to hold the module, and seal the enclosed area off from the outside. Oversized slots have been placed along the mating line of the shell halves, to encourage potting compound to flow into these areas and seal along the inside surface of the gasket, preventing the leakage that would otherwise occur along this mating line. Other flow gaps are placed inside the potting area to facilitate potting compound intrusion that seal the other structural ribs and mating surfaces. Thus, the gasket forms a seal, preferably airtight seal between the tray 36 and cover 34 when the device 30 is in a closed position.

Figure 14:
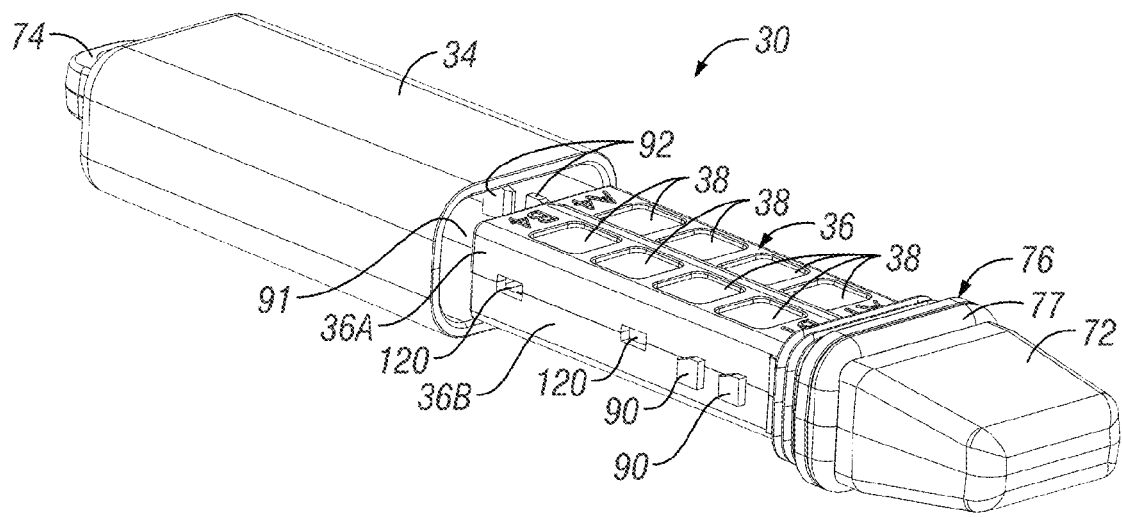
FIG. 14 is a perspective view of another embodiment of the device showing interlocking pins on both the tray and the interior of the cover of the device.

FIG. 14 is a perspective view of the integrated storage unit 30 in an open position with the tray 36 removed from the cover 34. Interlocking pins 20 are shown in the tray 36 while interlocking pins 92 are shown on the inside of the cover 34.

FIG. 15 illustrates the cover 34 with interlocking pins 92 on opposite sides of the case and in opposite orientations.

FIG. 16 illustrates the interlocking of pins 90, 92 functioning as a locking mechanism. In position 100 the cover is unlocked. In positions 102, 104, the cover is locked. The interlocking pins 92 are completely internal to the cover 34. The compression resistance of the gasket keeps the locking mechanism engaged, yet allows for unlocking when needed. Because the unlocking mechanism is internal to the device 30 when the device is in a closed position, the functionality of the device is not necessarily apparent. This may be advantageous in that because the cover removal feature is effectively hidden, children and others who have access to the device but are not in need of placing or retrieving a bio-sample are less likely to open the case. To open the case, a user may grasp the cover in one hand, the shoulder or gasket support rim of the tray with the other, and apply a counter-clock-wise twist (when viewed from either end), while gently pulling apart the cover and tray. Moreover, because two sets of interfering locking pins are used, accidental operation is likely to at best only partially open the device without exposing the dry chamber to air. Thus, it is not likely that the device is accidentally opened, or dropped upon accidental opening.

Figure 17:
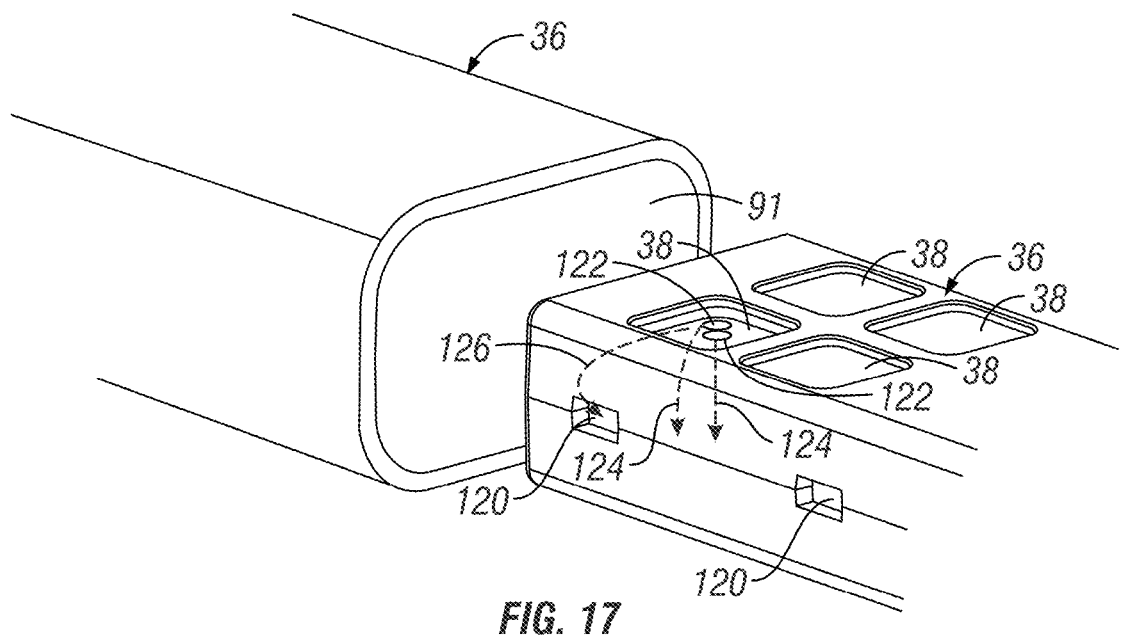
FIG. 17 illustrates air flow associated with the wells.

FIG. 17 illustrates air flow associated with the wells. Air paths 126 are shown for air exiting the wells 38, through the top side and around the housing and through holes 120. Similarly, air may pass through the underside of the wells 38 through holes 122 as illustrated with arrows 124. The air thus may circulate to the desiccant (not shown) which provides for removing the moisture from the air.

Figure 18:
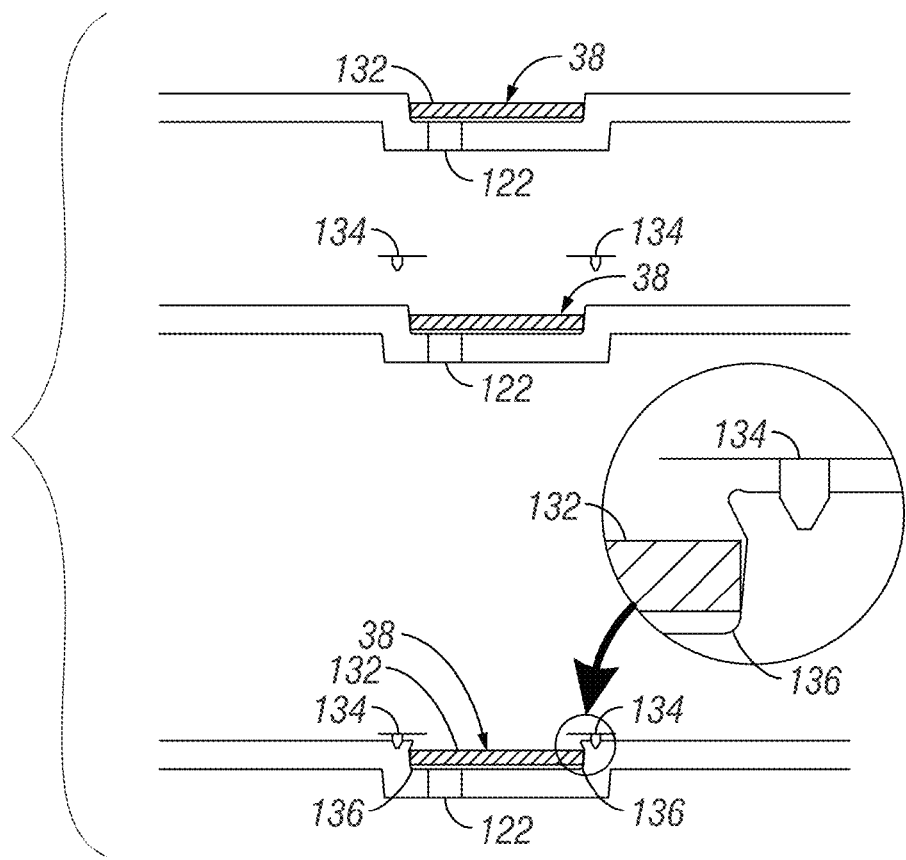
FIG. 18 illustrates cross sections of a well.

FIG. 18 illustrates cross sections of a well 38. The well 38 may have an air hole 122 associated with it, the air hole 122 positioned below the media 132 which may have a bio-sample thereon. The air hole 122 may assist in maintaining the bio-sample as dry by allowing some air space beneath the media. A tool 134 may also be used to deform plastic around the well 38 to provide edges 136 which extend over the material to assist in retaining the media and bio-sample in place. The present invention contemplates that where the edges of the well are deformed to assist in maintaining material in place, the edges of the wells may be deformed in various manners using various tools including by applying heat where the well is made from plastic. Thus, sample material may be held in place (in the wells) by heat-deforming (crimping) an annular pattern around the perimeter of the wells. This causes the material of the sides to deform, moving radially inward, such that the open end of the well physically constrains the sample material from falling out, yet does not clamp, deform, or otherwise stress the material. Intentional removal and replacement is possible using a probe, tweezers, or similar tool. The material may be held in place sufficiently to allow various methods of sample extraction to be performed successfully.

Figure 8:
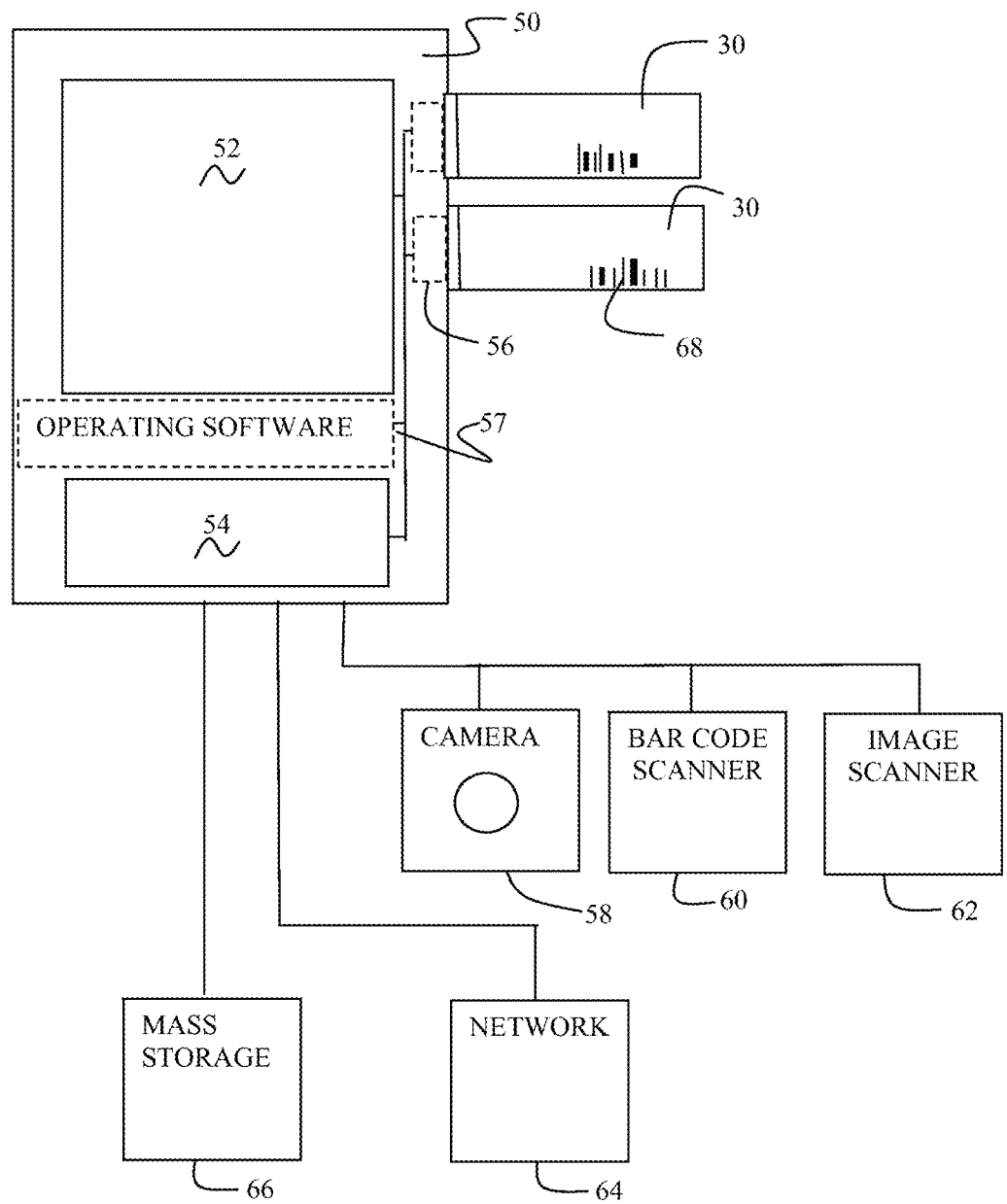
FIG. 8 is a block diagram of a data entry/extraction system employing the integral storage system as described for the embodiment herein.

FIG. 8 is a block diagram of an operational system for employing the integrated DNA and integrated digital data storage units of the disclosed embodiments. A microprocessor operated device or computer 50 such as a personal digital assistant (PDA), smart phone or laptop having a display 52 and integrated input device 54 such as a keyboard provides operational control of the system. An interface 56 for one or more integrated storage units 30 allows data transfer between the digital data storage units and the computer using operational software 57 residing on the computer. For the embodiment shown, standard USB interfaces may be employed for the digital data storage units with a configuration as described with respect to FIGS. 4-7 above. Additional peripherals such as a camera 58, bar code scanner 60, image scanner 62 and network interface 64 such as a wireless modem may be provided either as integral elements of the computer 50 or as separate devices interfaced with the computer using standard USB or other interface technology. Mass storage 66 associated with the computer allows integration of control software for specific applications of the digital data storage units as well as temporary or permanent storage of duplicate digital data stored on the integrated storage units. For the embodiment shown, each integrated storage unit 30 employs a bar code 68 for unique identification. The bar code scanner 60 associated with the computer 50 allows easy recognition of the integrated storage unit for data entry or download from/to the computer. The bar code 68 may be one-dimensional bar code, a two-dimensional bar code such as a QR code, Datamatrix, or other form of bar code or other machine readable identifier. In alternative embodiments, integrated digital identification in the digital data storage unit allows identification upon insertion into the interface on the computer or alternative unique readable indicia is provided on the unit. Exemplary applications the integrated DNA and digital data storage units of the disclosed embodiments with various configurations of the operational system may include child identification kits which could incorporate both a DNA sample bearing master unit, and an identical digital storage device as a traveler, either with additional DNA samples or a non-DNA bearing unit. Hospitals could initiate such child identification by taking samples after birth and entering initial physical descriptive data as well as birth certificate data. Hospitals could insert photographs, finger & feet prints, hospital records and family medical records. Hospitals may keep a duplicate unit on file, providing records for future contact with patient. Similarly, for pets and other veterinary applications DNA sample bearing units may be employed for medical and basic information which contain DNA, medical records, pictures and pedigree information. For breeders of pedigree animals the DNA sample bearing units could be used for demonstrating and storing valuable pedigree history and information. Plant growers may use DNA sample bearing units to allow tracking and storage of hybrid modification information.

Forensic science investigators could employ DNA sample bearing units and operational systems designed for crime scene investigative uses such as on-site collection of DNA and related evidence. Data and photographs taken directly from PDA or Laptop computer could be stored on the unit directly with the collected DNA samples. Similarly, in prisons and jail facilities DNA sample units with all related inmate information, records, photographs, etc. could be created upon entry processing and updated with additional data. One unit per individual accommodates following the individual through various facilities.

Individuals and agencies that periodically monitor various species in their natural habitat for endangered species verification and other similar uses could employ DNA sample bearing units with information and photograph storage. The storage units and operational system may be designed to allow for the range of variation in data taken for each species. Similarly, seed and biobanking conducted by universities, organizations, and businesses that are banking genetics for various reasons such as protecting heirloom, and early varieties of plants, seeds, and animals may use DNA sample bearing units designed to store information with each DNA sample.

Funeral homes could employ DNA sample bearing units for each decedent, and family history could then be inserted into the data storage. Such integrated storage could provide critical links to prior generations in the event of genetic illnesses or, conversely, if adequately developed, genetic restoration as gene therapy if mutation induced disease was encountered. Similarly, Genealogy societies and members could employ DNA sample bearing units to allow members to archive family DNA & history prior to the death of family members.

Figure 9:
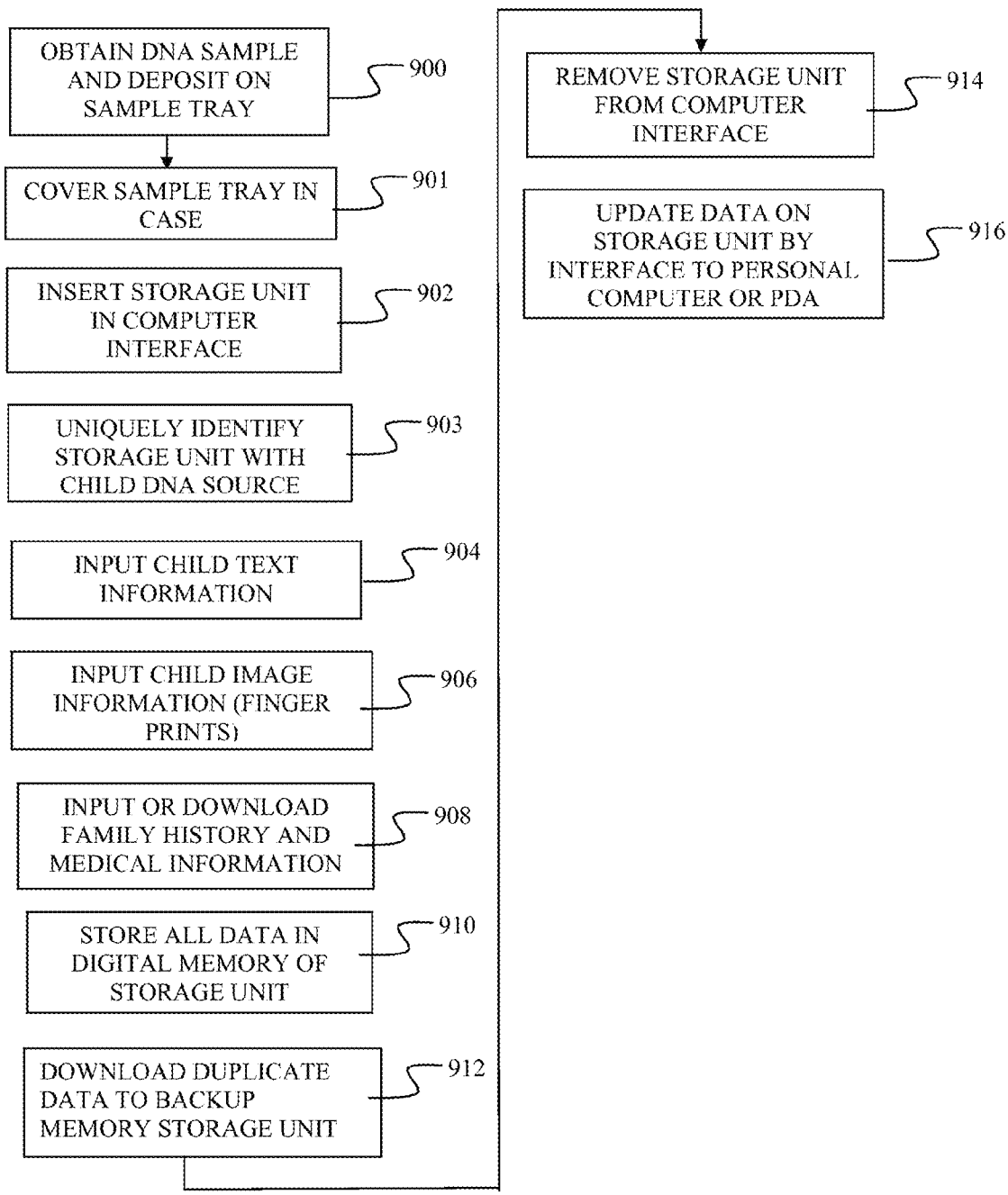
FIG. 9 is a flow chart of an exemplary operational method employed by the system of FIG. 8.

FIG. 9 is a flow chart for an exemplary process to accommodate the first example application of child identification using an operational system as disclosed with respect to FIG. 8. At the hospital at birth or at any other location in a subsequent child identification program DNA is obtained from the child through a blood draw or swab and deposited on the sample tray in an integrated storage unit, step 900. The sample tray is then covered by the case of the integrated storage unit, step 901. The digital data storage unit is inserted into the interface of the computer, step 902 and uniquely identified with the child using a bar code scanner 60 or internal digital identification, step 903. Input of the child's name and other information such as location, date and time of birth, birth weight, length, eye color, birth marks and parent identification are entered on the input device 54 of the computer 50, step 904. Finger, palm and foot prints may be taken in the convention manner and scanned as images into image scanner 60, step 906. In alternative systems, the image scanner may be employed to directly scan the hand and feet for input of identifying prints. Other related data such as family history and medical data may be entered using the input device or downloaded from mass storage 66 or network interface 64 as previously entered data, step 908. All data associated with the child received by the computer 50 is then stored in the digital memory 42 of the integrated storage unit 30, step 910. Duplicate data may then be downloaded into a second integrated storage unit, either with or without DNA storage, as a backup unit or for separate storage, step 912. Additional duplicates may be downloaded when the initial unit is created or subsequently if additional copies of the data are required. The integrated storage unit is then removed from the interface and is available for storage by the parents to maintain personal and identifying information of the child, step 914. Use of standard interfaces allows the integrated storage unit to also be updated with additional data by the parents, doctors, child care or school officials using standard personal computers or other devices equipped with interfacing operating software, step 916. For certain embodiments, any portion of the digital data may be encrypted and/or security protected to avoid overwriting or alteration. For example initial birth data and identifying information could be maintained in a secure portion of the memory with subsequently added data retained in a general purpose or random access portion of the memory.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A storage device, comprising:
a housing;
a non-volatile memory disposed within the housing;
an interface operatively connected to the housing for communicating with a computing device to provide access to the non-volatile memory to the computing device, wherein the interface is one of a standard USB and a standard SD flashcard;
a tray comprising a bio-sample storage area for storing bio-samples and further comprising a plurality of vent holes in the tray;
a gasket for sealing the bio-sample storage area within the housing for storage;
wherein in a closed position, the tray is sealed within the housing by the gasket and wherein in an open position, the bio-sample storage area is exposed and accessible.

2. The storage device of claim 1 wherein the housing comprises a cover with an interior chamber for receiving the tray.

3. The storage device of claim 2 further comprising a plurality of wells within the tray.

4. The storage device of claim 3 further comprising dry storage medium in each of the plurality of wells within the tray.

5. The storage device of claim 4 further comprising a desiccant disposed within the housing for removing moisture from air within the storage device when the storage device is in the closed position.

6. The storage device of claim 5 further comprising at least one hole at a bottom of each of the plurality of wells.

7. The storage device of claim 6 further comprising a plurality of interlocking pins on an interior wall of the cover and a plurality of interlocking pins on tray.

8. The storage device of claim 7 wherein the desiccant is chosen from the group consisting of charcoal, Silica Gel, Calcium Oxide, molecular sieve, clays and combinations thereof.

9. A storage device, comprising:
a housing;
a nonvolatile memory disposed within the housing;
an interface operatively connected to the housing for communicating with a computing device to provide access to the non-volatile memory to the computing device, wherein the interface is one of a standard USB and a standard SD flashcard;
a tray comprising a bio-sample storage area for storing bio-samples;
a plurality of wells within the tray;
dry storage media within each of the plurality of wells;
desiccant disposed within the housing for drying air within the housing;
a plurality of holes within the tray to assist in providing air flow.

10. The storage device of claim 9 further comprising a seal for sealing the tray within the housing.

11. The storage device of claim 10 wherein the seal comprises a gasket having a plurality of ridges.

12. The storage device of claim 11 further comprising a plurality of interlocking pins on an interior wall of the housing and a plurality of interlocking pins on the tray.

13. The storage device of claim 9 wherein desiccant is chosen from the group consisting of charcoal, Silica Gel, Calcium Oxide, molecular sieve, clays and combinations thereof.

14. A storage device, comprising:
a housing;
a non-volatile memory disposed within the housing;
an interface operatively connected to the housing for communicating with a computing device to provide access to the non-volatile memory to the computing device, wherein the interface is one of a standard USB and a standard SD flashcard;
a tray comprising a bio-sample storage area for storing bio-samples and further comprising a plurality of holes in the tray to allow for air flow;
a plurality of wells within the tray;
dry storage media within each of the plurality of wells;
desiccant disposed within the housing for drying air within the housing;
a gasket for sealing the bio-sample storage area within the housing for storage;
wherein in a closed position, the tray is sealed within the housing by the gasket and wherein in an open position, the bio-sample storage area is exposed;
a plurality of interlocking pins on an interior wall of the housing and a plurality of interlocking pins on the tray to interlock to lock the tray within the housing in the closed position.

15. The storage device of claim 14 wherein the desiccant is chosen from the group consisting of charcoal, Silica Gel, Calcium Oxide, molecular sieve, clays and combinations thereof.

16. The storage device of claim 14 further comprising a plurality of holes in the wells within the tray to allow for air flow.

* * * * *